(12) United States Patent
Craig

(10) Patent No.: US 7,074,811 B2
(45) Date of Patent: Jul. 11, 2006

(54) HYDROCHLORIDE SALTS OF 5-[4-[2-(N-METHYL-N-(2-PYRIDYL) AMINO)ETHOXY] BENZYL]THIAZOLIDINE-2,4-DIONE

(75) Inventor: Andrew Simon Craig, Tonbridge (GB)

(73) Assignee: SmithKline Beecham p.l.c., Brentford (GB)

( * ) Notice: Subject to any disclaimer, the term of this patent is extended or adjusted under 35 U.S.C. 154(b) by 311 days.

(21) Appl. No.: 10/221,686

(22) PCT Filed: Mar. 14, 2001

(86) PCT No.: PCT/GB01/01131
§ 371 (c)(1),
(2), (4) Date: Sep. 13, 2002

(87) PCT Pub. No.: WO01/68646
PCT Pub. Date: Sep. 20, 2001

(65) Prior Publication Data
US 2004/0152901 A1 Aug. 5, 2004

(30) Foreign Application Priority Data
Mar. 14, 2000 (GB) .............................. 0006133

(51) Int. Cl.
C07D 401/02 (2006.01)
A61K 31/44 (2006.01)

(52) U.S. Cl. .................................... 514/342; 546/269.7
(58) Field of Classification Search ................. 514/342; 546/269.7
See application file for complete search history.

(56) References Cited

U.S. PATENT DOCUMENTS

| | | | |
|---|---|---|---|
| 5,002,953 A | 3/1991 | Hindley | 514/275 |
| 5,708,012 A | 1/1998 | Olefsky | |
| 5,726,055 A | 3/1998 | Hindley et al. | 435/280 |
| 5,741,803 A | 4/1998 | Pool et al. | 514/342 |
| 5,910,592 A | 6/1999 | Pool et al. | 546/269.7 |
| 6,288,095 B1 | 9/2001 | Hindley | 514/367 |
| 6,664,278 B1 | 12/2003 | Sasse et al. | 514/342 |
| 2002/0137940 A1 | 9/2002 | Sasse et al. | 546/269.7 |
| 2003/0120078 A1 | 6/2003 | Sasse et al. | |

FOREIGN PATENT DOCUMENTS

| | | |
|---|---|---|
| CN | 1277965 | 12/2000 |
| EP | 0 306 228 | 3/1989 |
| WO | WO 94/05659 | 3/1994 |
| WO | WO 98/57634 | 12/1998 |
| WO | WO 00/63205 | 10/2000 |
| WO | WO 00/63206 | 10/2000 |
| WO | WO 00/64892 | 11/2000 |
| WO | WO 00/64893 | 11/2000 |
| WO | WO 00/64896 | 11/2000 |
| WO | WO 01/44240 | 6/2001 |
| WO | WO 02/20519 | 3/2002 |

OTHER PUBLICATIONS

H.G. Brittain. "Polymorphism in Pharmaceutical Solids", *Drugs and the Pharmaceutical Sciences*, 95:126–358 (1999).
Smith et al., "Treatment of Diabetes with Thiazolidinedione and Metformin". CA 130:61089 (WO 98/57634), 1998.
A.M. Rouhi. "The Right Stuff". *Chemical and Engineering News*, Feb. 24, 2003, pp. 32–34.
Cantello et al., "Facile Biocatalytic Reduction . . . Enantiomer and Analogues", *Journal of the Chemical Society*, Perkin Transactions 1, pp. 3319–3322 (1994).
Haleblian et al., "Pharmaceutical Applications of Polymorphism", *Journal of Pharmaceutical Sciences*, 58(8): 911–929 (1969).
H.G. Brittain. "Polymorphism in Pharmaceutical Solids", NY: Marcel Dekker, Inc. 1999, pp. 125–181, 183–226, 228–330.
J.R. Durbin, "Thiazolidinedione therapy in the prevention/delay of type 2 diabetes in patients with impaired glucose tolerance and insulin resistance," *Diabetes, Obesity and Metabolism*, 6, 280–285 (2004).

*Primary Examiner*—Zinna Northington Davis
(74) *Attorney, Agent, or Firm*—Kathryn L. Sieburth; Stephen Venetianer; Charles M. Kinzig

(57) ABSTRACT

A substantially non-hydrated and non-hygroscopic or slightly hygroscopic hydrochloride salt of 5-[4-[2-(N-methyl-N-(2-pyridyl)amino)ethoxy]benzyl]thiazolidine-2,4-dione; a pharmaceutical composition containing such a compound, a process of preparing such a compound and the use of such a compound in medicine.

17 Claims, 3 Drawing Sheets

HYDROCHLORIDE SALTS OF 5-[4-[2-(N-METHYL-N-(2-PYRIDYL) AMINO)ETHOXY] BENZYL]THIAZOLIDINE-2,4-DIONE

This invention relates to a novel pharmaceutical, to a process for the preparation of the pharmaceutical and to the use of the pharmaceutical in medicine.

European Patent Application, Publication Number 0,306, 228 relates to certain thiazolidinedione derivatives disclosed as having hypoglycaemic and hypolipidaemic activity. The compound of example 30 of EP 0,306,228 is 5-[4-[2-(N-methyl-N-(2-pyridyl)amino)ethoxy]benzyl]thiazolidine-2, 4-dione (hereinafter also referred to as "Compound I").

International Patent Application, Publication Number WO94/05659 discloses certain salts of the compounds of EP 0,306,228 and in particular the maleic acid salt.

It has now been discovered that Compound I forms a novel, non-solvated hydrochloride salt (hereinafter also referred to as the "Hydrochloride") that is particularly stable and hence is suitable for bulk preparation and handling. Surprisingly the Hydrochloride is indicated to be non-hygroscopic and shows good aqueous solubility. Moreover, the Hydrochloride is stable in aqueous solution and does not dissociate therein. It can also be prepared by an efficient, economic and reproducible process particularly suited to large-scale preparation.

The novel Hydrochloride also has useful pharmaceutical properties and in particular it is indicated to be useful for the treatment and/or prophylaxis of diabetes mellitus, conditions associated with diabetes mellitus and certain complications thereof.

Accordingly, the present invention provides 5-[4-[2-(N-methyl-N-(2-pyridyl)amino)ethoxy]benzyl]thiazolidine-2, 4-dione, hydrochloride characterised in that it:

(i) provides an infrared spectrum containing peaks at about 1745, 1516, 1257, 1056 and 803 $cm^{-1}$;
(ii) provides an X-ray powder diffraction (XRPD) pattern containing peaks at about 10.1, 13.4, 17.2, 22.2 and 29.4 °2θ; and/or
(iii) provides a Raman spectrum containing peaks at about 1314, 1242, 1185, 918 and 404 $cm^{-1}$.

Figure 1:
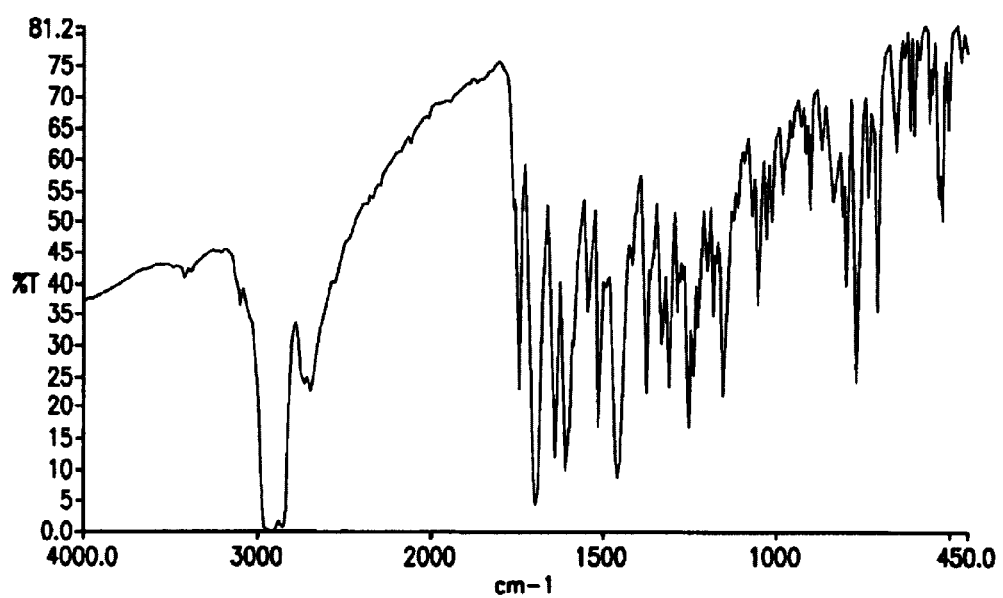
FIG. 1 is an infrared spectrum (liquid paraffin mull) of the Hydrochloride.
Figure 2:
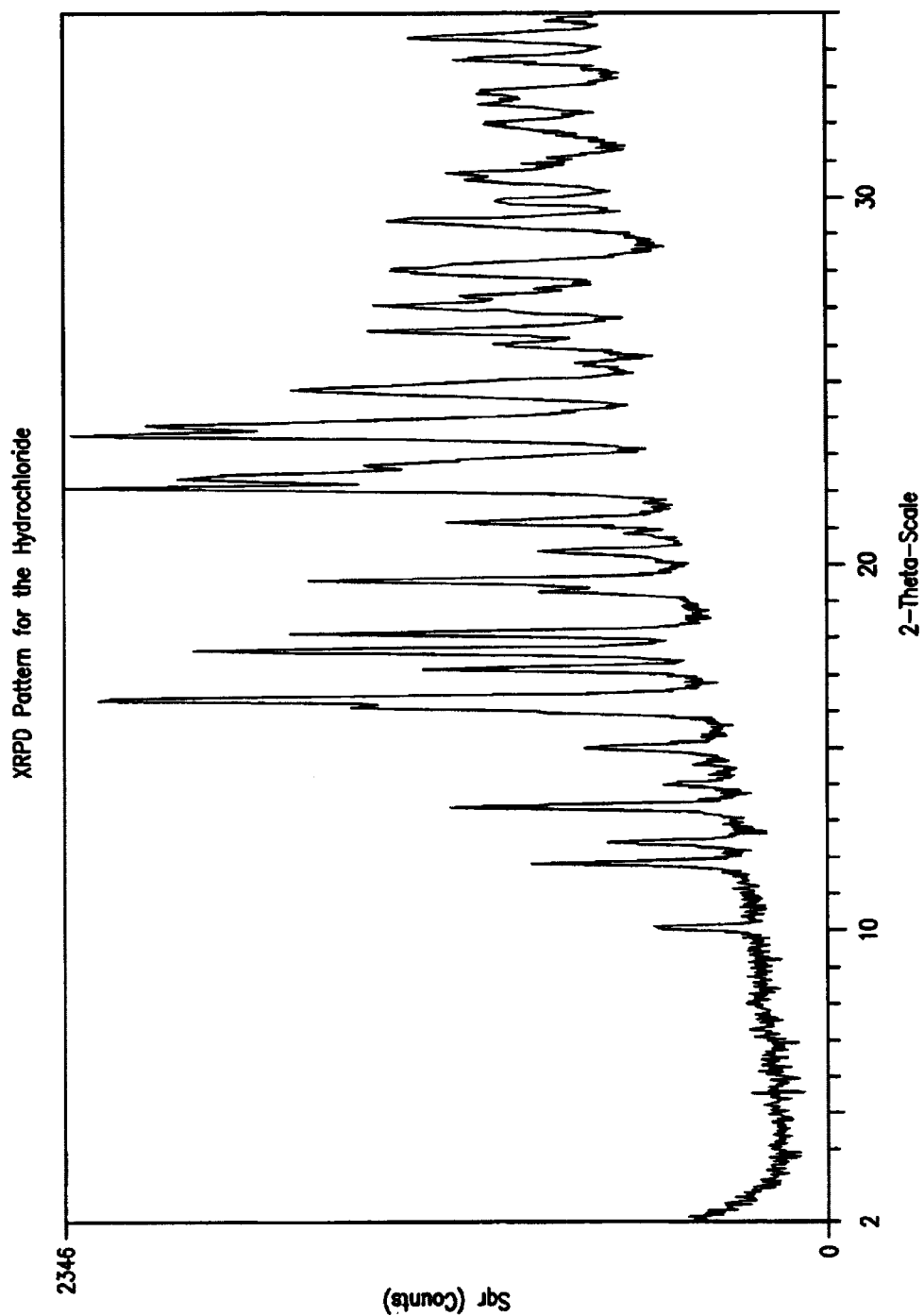
FIG. 2 is the X-ray powder diffraction pattern of Hydrochloride.
Figure 3:
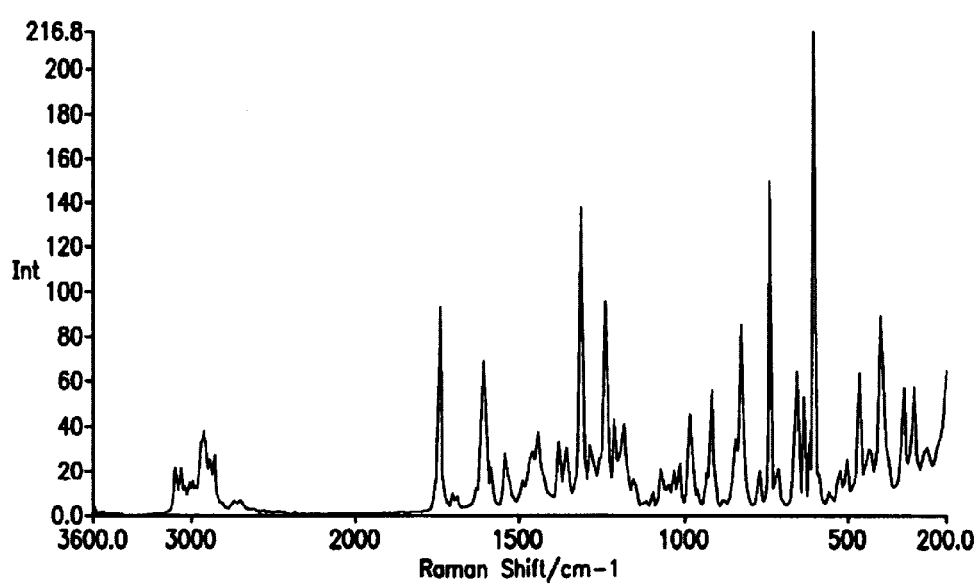
FIG. 3 is a Raman spectrum of the Hydrochloride.

In one favoured aspect, the Hydrochloride provides an infrared spectrum substantially in accordance with FIG. I.

In one favoured aspect, the Hydrochloride provides an X-Ray powder diffraction pattern (XRPD) substantially in accordance with FIG. II.

In a further aspect, the Hydrochloride provides a raman spectrum substantially in accordance with FIG. III.

The present invention encompasses the Hydrochloride isolated in pure form or when admixed with other materials.

Thus in one aspect there is provided the Hydrochloride in isolated form.

In a further aspect there is provided the Hydrochloride in pure form.

In yet a further aspect there is provided the Hydrochloride in crystalline form.

As indicated above the Hydrochloride is non-hygroscopic. The invention further includes substantially non-hydrated and non-hygroscopic (or slightly hygroscopic) hydrochloride salts of 5-[4-[2-(N-methyl-N-(2-pyridyl) amino)ethoxy]benzyl]thiazolidine-2,4-dione.

The invention also provides a process for preparing the Hydrochloride, characterised in that 5-[4-[2-(N-methyl-N-(2-pyridyl)amino)ethoxy]benzyl]thiazolidine-2,4-dione (Compound I) or a salt thereof, preferably dispersed or dissolved in a suitable solvent, is reacted with a source of hydrogen chloride; and thereafter the Hydrochloride is recovered.

Preferably, the reaction is carried out under anhydrous conditions, for example in a dried nitrogen atmosphere.

A suitable solvent is an alkanol, for example propan-2-ol, or a hydrocarbon, such as toluene, a ketone, such as acetone, an ester, such as ethyl acetate, an ether such as tetrahydrofuran, a nitrile such as acetonitrile, or a halogenated hydrocarbon such as dichloromethane.

Conveniently, the source of hydrogen chloride is a solution of hydrogen chloride in an appropriate solvent, usually the reaction solvent, for example propan-2-ol. Alternatively, the source of hydrogen chloride may be provided by concentrated hydrochloric acid or aqueous dilutions of concentrated hydrochloric acid which are suitably diluted so as to provide the required product, although concentrated hydrochloric acid is preferred.

It is considered that the Hydrochloride can be produced in the above mentioned reactions in the presence of small amounts of water but as stated the reaction is preferably carried out under anhydrous conditions.

The reaction is usually carried out at ambient temperature or at an elevated temperature, although any convenient temperature that provides the required product may be employed. A preferred temperature is in the range of from 20–120° C., such as 30° C. to 80° C., for example 70° C.

Recovery of the required compound generally comprises crystallisation from an appropriate solvent, conveniently the reaction solvent, usually by cooling to a temperature in the range of from 0° C. to 40° C., for example 20° C.

In one preferred form the recovery comprises initial cooling to a first temperature, such as 35° C. to 70° C., preferably 50° C. to 60° C., thereby allowing initiating crystallisation and thereafter cooling to a second temperature, suitably in the range of 0° C. to 40° C., to complete crystallisation.

Crystallisation can also be initiated by seeding with crystals of the Hydrochloride but this is not essential.

Compound I is prepared according to known procedures, such as those disclosed in EP 0,306,228 and WO94/05659. The disclosures of EP 0,306,228 and WO94/05659 are incorporated herein by reference.

When used herein the term prophylaxis of conditions associated with diabetes mellitus' includes the treatment of conditions such as insulin resistance, impaired glucose tolerance, hyperinsulinaemia and gestational diabetes.

When used herein the terms relating to hygroscopicity are used in accordance with known criteria as set out in J C Callahan et al., Drug Development and Industrial Pharmacy, 1982, 8(3), 355–69 which classifies hygroscopicity with respect to the % weight gain of a test compound under controlled conditions of temperature and humidity (25° C. and 75% relative humidity) wherein the test compound has been allowed to attain an approximately constant weight: the following classification is used:

| % Weight Gain | Classification |
| --- | --- |
| <2% | non-hygroscopic |
| 2–10% | slightly hygroscopic |
| 10–20% | moderately hygroscopic |
| >20% | very hygroscopic |

For the avoidance of doubt when used herein the terms "non-hygroscopic", "slightly hygroscopic", "moderately hygroscopic" and "very hygroscopic" are to have the meanings defined by the above mentioned criteria.

Furthermore, the term "slightly hygroscopic" can particularly mean a compound showing a % weight gain under the above mentioned criteria of any one of 2–9%. 2–8%, 2–7%, 2–6%, 2–5%, 2–4% and 2–3%.

Diabetes mellitus preferably means Type II diabetes mellitus.

Conditions associated with diabetes include hyperglycaemia and insulin resistance and obesity. Further conditions associated with diabetes include hypertension, cardiovascular disease, especially atherosclerosis, certain eating disorders, in particular the regulation of appetite and food intake in subjects suffering from disorders associated with under-eating, such as anorexia nervosa, and disorders associated with over-eating, such as obesity and anorexia bulimia. Additional conditions associated with diabetes include polycystic ovarian syndrome and steroid induced insulin resistance.

The complications of conditions associated with diabetes mellitus encompassed herein includes renal disease, especially renal disease associated with the development of Type II diabetes including diabetic nephropathy, glomerulonephritis, glomerular sclerosis, nephrotic syndrome, hypertensive nephrosclerosis and end stage renal disease.

As mentioned above the compound of the invention has useful therapeutic properties: The present invention accordingly provides the Hydrochloride for use as an active therapeutic substance.

More particularly, the present invention provides the Hydrochloride for use in the treatment and/or prophylaxis of diabetes mellitus, conditions associated with diabetes mellitus and certain complications thereof.

Hydrochloride may be administered per se or, preferably, as a pharmaceutical composition also comprising a pharmaceutically acceptable carrier. The formulation of the Hydrochloride is generally as disclosed for Compound I in the above mentioned publications.

Accordingly, the present invention also provides a pharmaceutical composition comprising the Hydrochloride and a pharmaceutically acceptable carrier therefor.

The Hydrochloride is normally administered in unit dosage form.

The active compound may be administered by any suitable route but usually by the oral or parenteral routes. For such use, the compound will normally be employed in the form of a pharmaceutical composition in association with a pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

As is common practice, the compositions will usually be accompanied by written or printed directions for use in the medical treatment concerned.

As used herein the term 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of diabetes mellitus, conditions associated with diabetes mellitus and certain complications thereof, in a human or non-human mammal which comprises administering an effective, non-toxic, amount of Hydrochloride to a human or non-human mammal in need thereof.

Conveniently, the active ingredient may be administered as a pharmaceutical composition hereinbefore defined, and this forms a particular aspect of the present invention.

In a further aspect the present invention provides the use of Hydrochloride for the manufacture of a medicament for the treatment and/or prophylaxis of diabetes mellitus, conditions associated with diabetes mellitus and certain complications thereof.

In the treatment and/or prophylaxis of diabetes mellitus, conditions associated with diabetes mellitus and certain complications thereof the Hydrochloride may be taken in amounts so as to provide Compound I in suitable doses, such as those disclosed in EP 0,306,228 and WO94/05659.

No adverse toxicological effects are indicated in the above mentioned treatments for the compounds of the invention.

The following examples illustrate the invention but do not limit it in any way.

EXAMPLE 1

Preparation of 5-[4-[2-(N-methyl-N-(2-pyridyl) amino)ethoxy]benzyl]thiazolidine-2,4-dione hydrochloride A mixture of 5-[4-[2-(N-methyl-N-(2-pyridyl)amino) ethoxy]benzyl]thiazolidine-2,4-dione (6.0 g) and propan-2-ol (120 ml) was stirred and heated to 50° C. under a nitrogen atmosphere. A solution of hydrogen chloride in propan-2-ol (5–6 N, 5.0 ml) was added and the stirred mixture warmed to 70° C., at which point a clear solution was observed. After cooling to 45° C. over a period of one hour the resulting cloudy solution was warmed to 60° C. and maintained at this temperature for a period of 1 hour. The resulting thick white suspension was cooled to 30° C. and the solid product collected by filtration, washed with propan-2-ol (25 ml) and dried under vacuum, over phosphorus pentoxide for 16 hours to give the title compound as a white crystalline solid (5.7 g).

Melting point 168–170° C.

DSC: $T_{onset}$=166.6° C., $T_{peak}$=169.5° C.

| Elemental Analysis: | | | |
|---|---|---|---|
| Found: | C; 54.88 | H; 5.16 | N; 10.56 |
| Theory: ($C_{18}H_{20}N_3O_3SCl$) | C; 54.89 | H; 5.12 | N; 10.67 |

Ionic chlorine: Determined as 9.0% wt/wt (theory for $C_{18}H_{20}N_3O_3SCl$: 9.0% wt/wt).

Water content: Determined as 0.2% wt/wt using a Karl Fischer apparatus.

EXAMPLE 2

Preparation of 5-[4-[2-(N-methyl-N-(2-pyridyl) amino)ethoxy]benzyl]thiazolidine-2,4-dione hydrochloride A mixture of 5-[4-[2-(N-methyl-N-(2-pyridyl)amino) ethoxy]benzyl]thiazolidine-2,4-dione (4.0 g) and propan-2-ol (100 ml) was stirred and heated to 70° C. Concentrated hydrochloric acid (1.1 ml) was added to the stirred reaction mixture which was observed to give a clear solution after approximately 3 minutes. The stirred solution was cooled to 58° C. and then maintained at a temperature between 58–60° C. for 1 hour. The resulting white suspension was cooled to 30° C. and the solid product collected by filtration, washed with propan-2-ol (20 ml) and dried under vacuum over phosphorus pentoxide for 64 hours to give the title compound as a white crystalline solid (4.3 g).

Hygroscopicity of the Hydrochloride

A sample of the hydrochloride salt (279 mg), prepared according to Example 1, was exposed to a 75% relative humidity atmosphere at 21° C. for a period of 43 days. The sample attained constant weight during this period. The percentage weight gain of the sample was observed to be 0.4%.

Conclusion

The hydrochloride salt is non-hygroscopic.

Aqueous Stability and Solubility of the Hydrochloride 50 mg of the salt was placed in a 20 mL volumetric flask, and water added in 2.5 mL aliquots. The sample was ultrasonicated at 21° C. to aid dissolution after each subsequent addition of water and then examined. When a clear solution was obtained, the approximate solubility mg/mL was calculated. The solution was then examined at hourly intervals for evidence of subsequent clouding or precipitation.

| Water added total (mL) | Observation |
|---|---|
| 2.5 mL | Cloudy suspension |
| 5.0 mL | Predominantly clear, only partially cloudy |
| 7.5 mL | Clear solution obtained. Remained clear after standing at 21° C. for a further 2 hours. Approx. solubility 7 mg/mL |

Conclusion

The white crystalline solid dissolved readily to give a clear solution with a good aqueous solubility. The solution subsequently remained clear with no evidence of precipitation or clouding of the solution. This data confirms a previous experiment on a different batch of the Hydrochloride that also evidenced good solubility and provided a clear solution with no evidence of precipitation or clouding of the solution Characterising Data Recorded for the Product of Example 1:

A Infrared

The IR spectrum (FIG. I) was recorded as a liquid paraffin mull using a Perkin-Elmer 1720x FTIR instrument at a resolution of 2 cm–1. The spectrum obtained is shown in FIG. I. Bands were observed at:

1745, 1696, 1641, 1609, 1544,1516, 1331, 1313, 1289, 1257, 1243, 1230, 1203, 1185, 1157, 1073, 1056, 1032, 1015, 984, 918, 907, 873, 841, 811, 803, 772, 738, 714, 657, 618, 605, 560, 527 and 505 $cm^{-1}$.

B X-Ray Powder Diffraction (XRPD)

The XRPD pattern of the Hydrochloride (FIG. II) was recorded using a using the following acquisition conditions: Tube anode: Cu, Generator tension: 40 kV, Generator current: 40 mA, Start angle: 2.0 °2θ, End angle: 35.0 °2θ, Step size: 0.02 °2θ, Time per step: 10.0 seconds.

Characteristic XRPD angles and relative intensities are recorded in Table I.

TABLE I

| Diffraction Angle (° 2θ) | Relative Intensity (%) |
| --- | --- |
| 10.1 | 4.9 |
| 11.8 | 15.2 |
| 12.4 | 8.1 |
| 13.4 | 24.7 |
| 14.0 | 4.5 |
| 14.6 | 2.6 |
| 15.0 | 10 |
| 16.1 | 38.2 |
| 16.3 | 91.6 |
| 17.2 | 28 |
| 17.7 | 69 |
| 18.1 | 49.5 |
| 19.3 | 14.2 |
| 19.6 | 46.1 |
| 20.4 | 14.2 |
| 20.9 | 6.9 |
| 21.2 | 24.9 |
| 22.2 | 100 |
| 22.4 | 72.5 |
| 22.7 | 36.4 |
| 23.6 | 98.2 |
| 23.8 | 79.8 |
| 24.8 | 49.1 |
| 25.5 | 10.6 |
| 26.1 | 18.9 |
| 26.4 | 35.9 |
| 27.1 | 35.2 |
| 27.4 | 22.9 |
| 28.1 | 32.6 |
| 29.4 | 32.9 |
| 30.0 | 18.8 |
| 30.6 | 21.4 |
| 31.1 | 11.8 |
| 32.1 | 20 |
| 32.6 | 20.5 |
| 33.0 | 19.8 |
| 33.9 | 23.5 |
| 34.5 | 29.6 |

C Raman

The Raman spectrum (FIG. III) was recorded with the sample in a glass vial in a Perkin-Elmer 2000R FT-Raman system, at 4 cm$^{-1}$ resolution. Excitation was from a Nd:YAG laser (1064 nm) with a power output of 400 mW. Bands were observed at:
3100, 3068, 2927, 2893, 2863, 1746, 1706, 1611, 1587, 1545, 1446, 1382, 1360, 1314, 1287, 1242, 1212, 1185, 1156, 1096, 1073, 1032, 1017, 984, 918, 828, 772, 741, 715, 659, 636, 619, 606, 527, 506, 471, 440, 404, 333, 302, 262 cm$^{-1}$.

What is claimed is:

1. A compound which is 5-[4-[2-(N-methyl-N-(2-pyridyl)amino)ethoxy]benzyl]thiazolidine-2,4-dione hydrochloride, wherein said compound provides at least one of:
   (i) an infrared spectrum containing peaks at about 1745, 1516, 1257, 1056 and 803 cm$^{-1}$.
   (ii) an X-ray powder diffraction pattern containing peaks at about 10.1, 13.4, 17.2, 22.2 and 29.4 °2θ; and
   (iii) a Raman spectrum containing peaks at about 1314, 1242, 1185, 918 and 404 cm$^{-1}$.

2. A compound which is 5-[4-[2-(N-methyl-N-(2-pyridyl)amino)ethoxy]benzyl]thiazolidine-2,4-dione hydrochloride, wherein said compound, in a liquid paraffin mull, provides an infrared spectrum substantially in accordance with Figure I.

3. A compound which is 5-[4-[2-(N-methyl-N-(2-pyridyl)amino)ethoxy]benzyl]thiazolidine-2,4-dione hydrochloride, wherein said compound provides an X-Ray powder diffraction pattern substantially in accordance with Figure II.

4. A compound which is 5-[4-[2-(N-methyl-N-(2-pyridyl)amino)ethoxy]benzyl]thiazolidine-2,4-dione hydrochloride, wherein said compound provides a Raman spectrum substantially in accordance with Figure III.

5. A process for preparing the compound according to claim 1 comprising
   forming a dispersion or a solution of 5-[4-[2-(N-methyl-N-(2-pyridyl)amino)ethoxy]benzyl]thiazolidine-2,4-dione or a salt thereof, in a suitable solvent;
   treating said dispersion or solution of 5-[4-[2-(N-methyl-N-(2-pyridyl)amino)ethoxy]benzyl]thiazolidine-2,4-dione or a salt thereof, with a source of chloride ion; and
   recovering the compound.

6. A pharmaceutical composition comprising the compound according to claim 1 and a pharmaceutically acceptable carrier therefor.

7. A pharmaceutical composition comprising the compound according to claim 2 and a pharmaceutically acceptable carrier therefor.

8. A pharmaceutical composition comprising the compound according to claim 3 and a pharmaceutically acceptable carrier therefor.

9. A pharmaceutical composition comprising the compound according to claim 4 and a pharmaceutically acceptable carrier therefor.

10. A method of treatment of diabetes mellitus, conditions associated with diabetes mellitus and certain complications thereof, comprising administering an effective amount of the compound according to claim 1 to a human or non-human mammal in need thereof.

11. A method of treatment of diabetes mellitus, conditions associated with diabetes mellitus and certain complications thereof, comprising administering an effective amount of the compound according to claim 2 to a human or non-human mammal in need thereof.

12. A method of treatment of diabetes mellitus, conditions associated with diabetes mellitus and certain complications thereof, comprising administering an effective amount of the compound according to claim 3 to a human or non-human mammal in need thereof.

13. A method of treatment of diabetes mellitus, conditions associated with diabetes mellitus and certain complications thereof, comprising administering an effective amount of the compound according to claim 4 to a human or non-human mammal in need thereof.

14. A method of treatment of Type II diabetes comprising administering an effective amount of the compound according to claim 1 to a human or non-human mammal in need thereof.

15. A method of treatment of Type II diabetes comprising administering an effective amount of the compound according to claim 2 to a human or non-human mammal in need thereof.

16. A method of treatment of Type II diabetes comprising administering an effective amount of the compound according to claim 3 to a human or non-human mammal in need thereof.

17. A method of treatment of Type II diabetes comprising administering an effective amount of the compound according to claim 4 to a human or non-human mammal in need thereof.

* * * * *